US006989027B2

(12) United States Patent
Allen et al.

(10) Patent No.: US 6,989,027 B2
(45) Date of Patent: Jan. 24, 2006

(54) PERCUTANEOUSLY DELIVERED TEMPORARY VALVE ASSEMBLY

(75) Inventors: Jeffrey W. Allen, Santa Rosa, CA (US); David S. Brin, Topsfield, MA (US); Chris M. Coppin, Carlsbad, CA (US)

(73) Assignee: Medtronic Vascular Inc., Santa Rosa, CA (US)

( * ) Notice: Subject to any disclaimer, the term of this patent is extended or adjusted under 35 U.S.C. 154(b) by 0 days.

(21) Appl. No.: 10/835,153

(22) Filed: Apr. 29, 2004

(65) Prior Publication Data

US 2004/0225354 A1 Nov. 11, 2004

Related U.S. Application Data

(60) Provisional application No. 60/466,938, filed on Apr. 30, 2003.

(51) Int. Cl.
*A61F 2/06* (2006.01)
(52) U.S. Cl. .................................. 623/2.18; 606/200
(58) Field of Classification Search ............... 606/200; 623/1.12, 904, 2.18
See application file for complete search history.

(56) References Cited

U.S. PATENT DOCUMENTS

| 3,671,979 | A | | 6/1972 | Moulopoulos |
| 4,056,854 | A | | 11/1977 | Boretos et al. |
| 4,339,831 | A | | 7/1982 | Johnson |
| 4,705,507 | A | | 11/1987 | Boyles |
| 5,545,214 | A | | 8/1996 | Stevens |
| 6,551,303 | B1 | * | 4/2003 | Van Tassel et al. ......... 604/508 |
| 2002/0151970 | A1 | | 10/2002 | Garrison et al. |
| 2003/0109921 | A1 | * | 6/2003 | Moe et al. ................. 623/2.11 |
| 2005/0004652 | A1 | * | 1/2005 | van der Burg et al. .... 623/1.12 |
| 2005/0010285 | A1 | * | 1/2005 | Lambrecht et al. ........ 623/2.18 |
| 2005/0015112 | A1 | * | 1/2005 | Cohn et al. ................. 606/200 |
| 2005/0049573 | A1 | * | 3/2005 | Van Tassel et al. ......... 604/508 |

FOREIGN PATENT DOCUMENTS

FR 2728457 6/1996
WO WO 00/44313 8/2000

\* cited by examiner

*Primary Examiner*—Suzette J-J Gherbi (57) ABSTRACT

The percutaneously delivered temporary valve assembly of the present invention, and method of using the same, provides an elongate element and a temporary valve disposed on the elongate element. The temporary valve can comprise struts and a membrane attached to the struts. The elongate element can include at least one lumen. The percutaneously delivered temporary valve assembly can be used to replace an aortic valve by locating a temporary valve in a patient's ascending aorta; deploying the temporary valve; removing the native aortic valve past the temporary valve; implanting the prosthetic aortic valve past the temporary valve; collapsing the temporary valve; and removing the temporary valve from the patient. The temporary valve can be sized to the patient and can be left in place while the prosthetic aortic valve heals in.

38 Claims, 11 Drawing Sheets

FIG. 11

PERCUTANEOUSLY DELIVERED TEMPORARY VALVE ASSEMBLY

RELATED APPLICATION

This application claims priority to U.S. Provisional Application No. 60/466,938, "Percutaneously Delivered Temporary Valve" to Jeffrey W. Allen, et al., filed Apr. 30, 2003, the entirety of which is incorporated by reference.

TECHNICAL FIELD

The technical field of this disclosure is medical devices, particularly, a percutaneously delivered temporary valve assembly and method of using the same.

BACKGROUND OF THE INVENTION

Heart valves, such as the aortic valve, are sometimes damaged by diseases or by aging which can cause problems with the proper function of the valve. Heart valve disease generally takes one of two forms: stenosis, in which a valve does not open completely or the opening is too small, resulting in restricted blood flow; or insufficiency, in which blood leaks retrograde across the valve that should be closed. Valve replacement may be required in severe cases to restore cardiac function. In common practice, replacement requires open-heart surgery with its attendant risks, expense, and extended recovery time. Open-heart surgery also requires cardiopulmonary bypass with risk of thrombosis, stroke, and infarction.

Catheter based valve replacement has been proposed as a way to effect valve replacement percutaneously and to avoid open-heart surgery. Such procedures involve excision of the native valve and replacement of the native valve with a prosthetic valve, or installation of a prosthetic valve over the native valve. To avoid cardiopulmonary bypass, the catheter based valve replacement is performed on a beating heart. Following excision of the native valve, no valve is present to preserve the pumping action of the heart while the permanent prosthetic valve is being implanted.

An additional consideration in both open-heart and catheter based valve replacement is the healing process after the prosthetic valve is implanted. After the valve replacement procedure, scar tissue must form around the sewing cuff to secure the prosthetic valve in position. In current practice, multiple knotted sutures anchor the prosthetic valve in place until ingrowth of scar tissue into the sewing cuff takes over the load bearing function. However, the placement of knotted sutures by catheter can be very difficult and time consuming.

Artificial heart valves for temporary use are known in the art, but present certain problems. Some designs are complex, inflating and deflating balloons to alternately block and permit flow. Such designs require complex sensing and control systems. Other designs fail to provide access for tools that must reach the valve site for removal of the native valve and placement of the prosthetic valve. Yet other designs require elaborate supporting frames to hold the valve portion.

U.S. Pat. No. 3,671,979 to Moulopoulos discloses an artificial heart valve for implantation in close proximity to a malfunctioning or damaged natural aortic or mitral heart valve by remote means without performing an open chest or other major surgical operation, the artificial heart valve comprising a flexible membrane in the form of an umbrella.

U.S. Pat. No. 4,056,854 to Boretos et al. discloses an artificial valve remotely placeable in a blood vessel without major surgery to supplant the function of a malfunctioning natural valve including an expansible check valve remotely placed in a constricted configuration through the vessel and a remotely removable constraint for selective expansion of the check valve for sealing engagement thereof within the walls of the vessel at the desired location.

U.S. Pat. No. 4,705,507 to Boyles discloses an arterial catheter of the multi-lumen type having an inflatable balloon portion to wedge the catheter in place against the arterial wall. Multi-infusions are allowed through the segmented multi-lumens. The catheter is designed to allow blood to flow in the arterial system with the catheter in place. During diastolic phases, the blood flow will be closed off with movable plastic valves.

U.S. patent application No. 20020151970 to Garrison et al. discloses a valve implantation system having a valve displacer for displacing and holding the native valve leaflets open wherein a replacement valve may be attached to the valve displacer before or after introduction and may be positioned independent of the valve displacer and wherein a temporary valve mechanism may be used to provide temporary valve functions during and after deployment of the valve displacer.

WIPO International Publication No. WO 00/44313 to Lambrecht et al. discloses temporary valve devices with one or more cannulae which guide insertion of the valve into the aorta. The valve devices expand in the aorta to occupy the entire flow path of the vessel. In one embodiment, the temporary valve has leaflets which act in concert to alternately block or allow blood flow.

It would be desirable to have a percutaneously delivered temporary valve that would overcome the above disadvantages.

SUMMARY OF THE INVENTION

One aspect of the present invention provides a percutaneously delivered temporary valve to provide valve function during valve replacement.

Another aspect of the present invention provides a percutaneously delivered temporary valve to permitting access for tools at the valve site during valve replacement.

Another aspect of the present invention provides a percutaneously delivered temporary valve to supplement valve function after valve replacement.

Another aspect of the present invention provides a percutaneously delivered temporary valve to provide load relief until adequate scar tissue ingrowth has taken place around a prosthetic valve after valve replacement.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENT

Figure 1A:
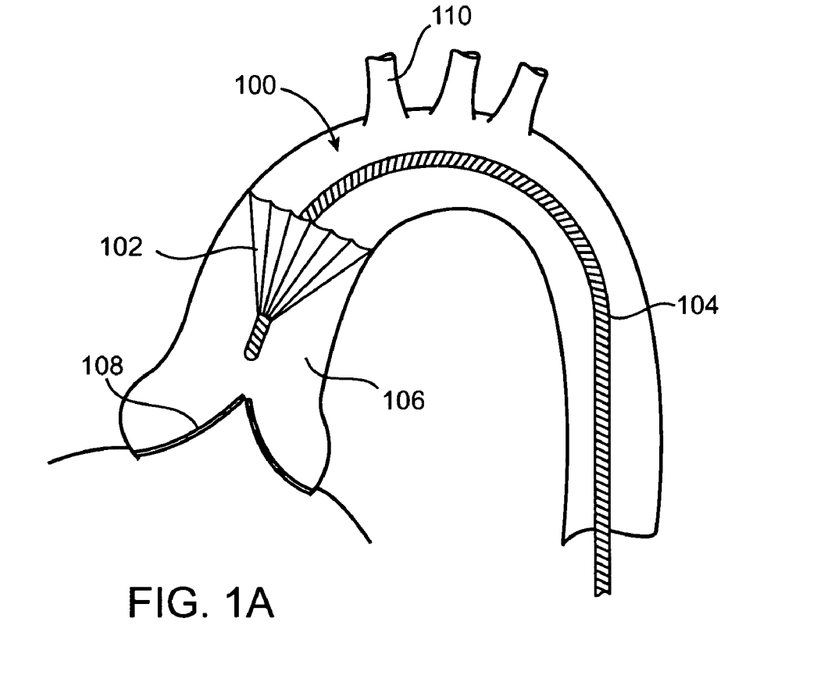
FIGS. 1A–1C show a percutaneously delivered temporary valve system made in accordance with the present invention.
Figure 1B:
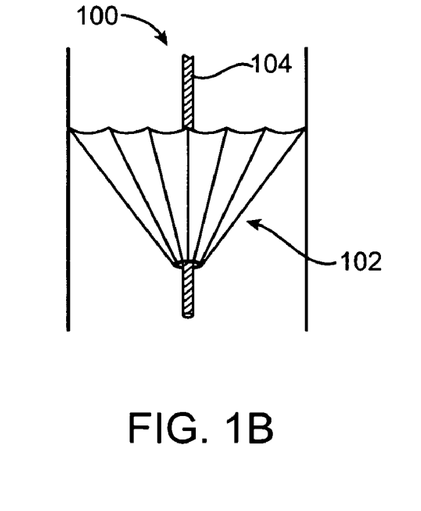
Figure 1C:
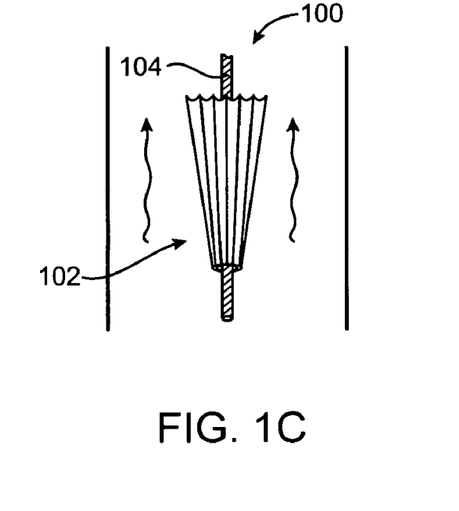

FIGS. 1A–1C, in which like elements share like reference numbers, shows a percutaneously delivered temporary valve system. FIG. 1A shows the temporary valve disposed in the ascending aorta, and FIGS. 1B & 1C show the temporary valve during diastole and systole, respectively. In one embodiment, the Referring to FIG. 1A, the temporary valve system 100 comprises a temporary valve 102 connected to an elongate element 104. In the example shown, the temporary valve 102 is located in the ascending aorta 106 between the aortic valve 108 and the brachiocephalic artery 110. FIG. 1B shows the temporary valve 102 in the open position seating against the aortic wall to block retrograde blood flow during diastole. FIG. 1C shows the temporary valve 102 in the closed position at a reduced diameter to allow anterograde blood flow during systole. The temporary valve 102 alternates passively between the open and closed positions in response to the differential pressure across the valve. In one embodiment, the temporary valve 102 is an umbrella-like valve and the elongate element 104 includes at least one lumen.

Figure 2:
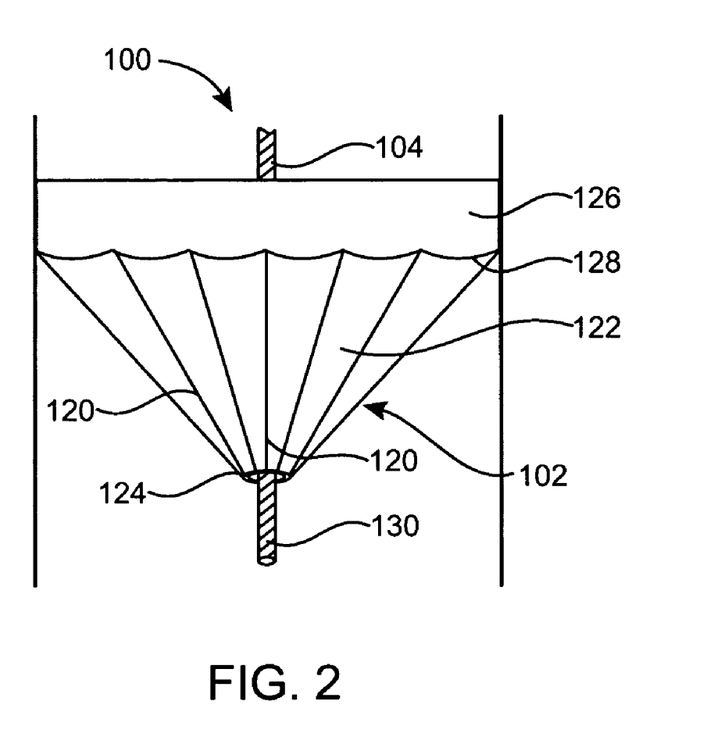
FIG. 2 shows a detailed view of a percutaneously delivered temporary valve made in accordance with the present invention.

FIG. 2 shows a detailed view of a percutaneously delivered temporary valve made in accordance with the present invention. The temporary valve 102 comprises struts 120 and a membrane 122 attached to the struts 120. The temporary valve 102 can be attached to the elongate element 104 at the valve apex 124 with the distal end of the temporary valve 102 pointed toward the heart in the direction of normal flow. An optional skirt 126 can be attached at the seating edge 128 of the temporary valve 102 to provide additional sealing surface against the vessel wall.

Those skilled in the art will appreciate that the elements of the temporary valve 102 can be joined in a number of ways. The struts 120 can be located on the outside or the inside of the membrane 122, or can be internal to or fabricated as part of the membrane 122. The membrane 122 can be attached to the struts 120 with adhesive, by sewing with a wire or fiber filament, or by a combination of such methods. Flow at the valve apex 124 can be prevented by sealing the membrane 122 at the valve apex 124 with a sealant or adhesive, by tying or wrapping the membrane 122 with a wire or fiber filament, or by a combination of such methods.

The temporary valve 102 can be located on the elongate element 104 at a distance from the distal tip 130 so that the temporary valve 102 is located in the ascending aorta during use. In one embodiment, the temporary valve 102 is between about 1 and 8 centimeters from the distal tip 130, and more particularly at about 5 centimeters.

The membrane 122 can be any flexible, collapsible sheet material, which is generally impermeable to flow, biocompatible, and non-thrombogenic. Examples of suitable synthetic polymers and co-polymers include, but are not limited to, segmented polyurethane with a small percentage of added silicone, reinforced polyurethane, coated nylon such as sheeted, non-braided coated nylon, and the like. The membrane 122 can also be made of a fixed collagenous membrane of animal origin, such as pericardium, or a membrane generated synthetically through recombinant DNA technology in yeast. In one embodiment, the membrane 122 can be coated with an anti-thrombotic material to further enhance biocompatibility. The anti-thrombotic material can be a natural molecule, such as heparin, or synthetics, such as the conducting polymer polypirrole.

The struts 120 can be hinged at the elongate element 104 or fixedly attached to the elongate element 104. In one embodiment, the struts 120 can be rigid and hinges provided where each strut 120 meets the elongate element 104 at the valve apex 124: the hinge allows the temporary valve 102 to alternate between the open and closed position. The hinge can be a separate element connecting the struts 120 to the elongate element 104, or can be a portion of the flexible membrane 122 between the struts 120 and the elongate element 104. In another embodiment, the struts 120 can be flexible and fixedly attached the elongate element 104: the struts 120 flex to allow the temporary valve 102 to alternate between the open and closed position.

The struts 120 can be rigid or flexible depending on the particular application. Examples of suitable materials include, but are not limited to, titanium, stainless steel, shape memory alloys such as nitinol, hard plastic such as polypropylene, or the like. The struts 120 can be straight or curved, and can perform multiple functions, such as both maintaining the geometry of the membrane 122 and centering the elongate element 104 within the aorta. Struts of different shapes, materials and flexibilities can be combined in a single temporary valve. For example, less flexible struts can alternate with flexible struts. The less flexible struts hold the temporary valve in position against the aortic wall and center the elongate element, while the flexible struts move in response to the heart pumping to alternately block and allow blood flow through the temporary valve. The number of struts 120 can be varied as required for a particular application.

The elongate element 104 can be a catheter, guide wire, or any other elongate element to deliver the temporary valve 102 into a vessel lumen where temporary valve function is required. In one example, the elongate element 104 can be inserted inguinally into the femoral artery and advanced until the distal end carrying the temporary valve 120 is in the ascending aorta near the aortic valve. The elongate element 104 can have a solid cross section, or can include one or more lumens extending the length or the partial length of the elongate element 104. A lumen from the proximal end of the elongate element 104 to the distal tip 130 can provide access from outside the patient, past the temporary valve, to the work area at the heart or heart valve. The lumens can be used for inserting tools, injecting chemicals, sampling fluids, inserting sensors and sensor cables, or actuating the temporary valve with fluids, gases, electrical cables, or wires. The elongate element 104 can be preformed to a curved shape which will more easily follow the curves of the body lumen into which the elongate element 104 is inserted. The distal tip 130 can be tilted at a fixed angle to the long axis of the elongate element 104, or steerable, to direct the distal tip 130 toward the work area. The elongate element 104 can also carry additional elements along its length, such as filters to retain embolic material, or centering balloons or fingers to center the elongate element 104 in the body lumen. One or more radiopaque markers can be provided on the elongate element 104 for location of the temporary valve assembly by fluoroscopy during use.

The optional skirt 126 can provide additional sealing surface against the aortic wall and can protect the aortic wall from the tips of the struts 120 at the seating edge 128. The skirt 126 can be the same or different material than the membrane 122. Exemplary materials for the skirt 126 include the materials used in the membrane 122, such as segmented polyurethane with a small percentage of added silicone, reinforced polyurethane, coated nylon such as sheeted, non-braided coated nylon, fixed collagenous membrane of animal origin, and the like. In another embodiment, the skirt 126 can be made of soft silicone. The skirt 126 can be thicker than the membrane 122 and can have a defined profile, such as circumferential external ribbing, to increase sealing at the aortic wall. In one embodiment, the skirt 126 can be a conformable, slightly stiff cuff. In another embodiment, the skirt 126 can be inflatable. In another embodiment, the skirt 126 can provide padding between the ends of the struts and the aortic wall to protect the aortic wall.

Figure 3A:
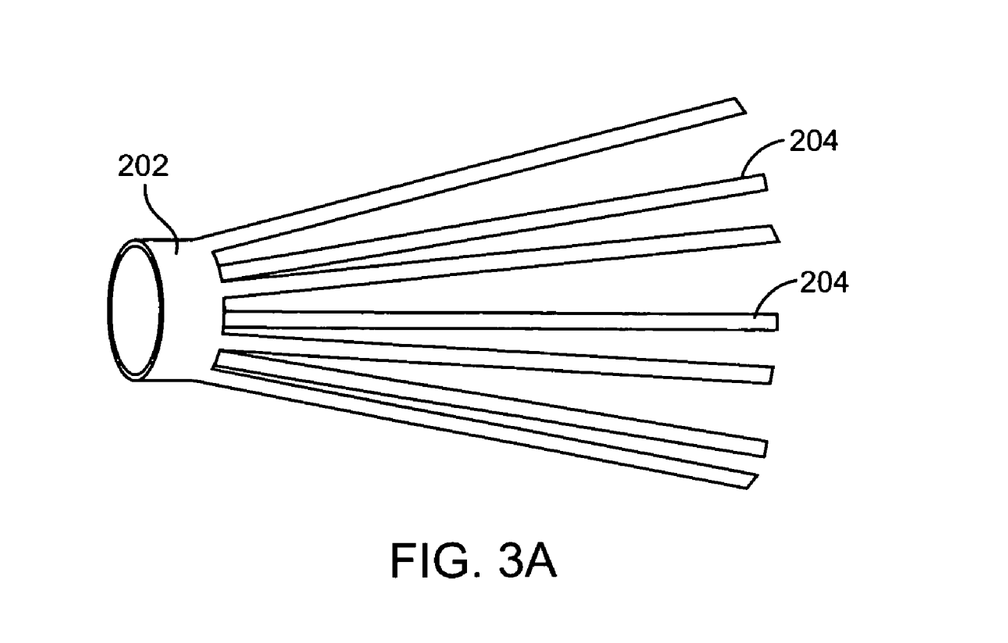
FIGS. 3A–3C show embodiments of a strut assembly for a percutaneously delivered temporary valve made in accordance with the present invention.
Figure 3B:
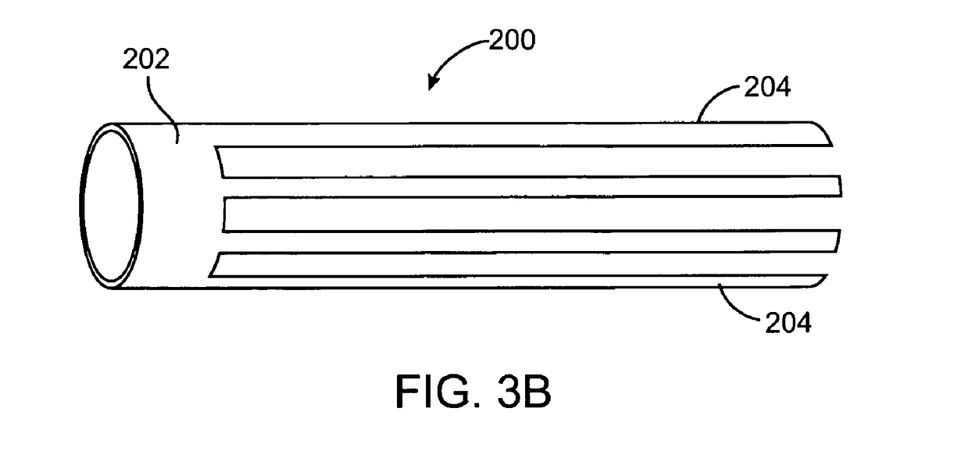
Figure 3C:
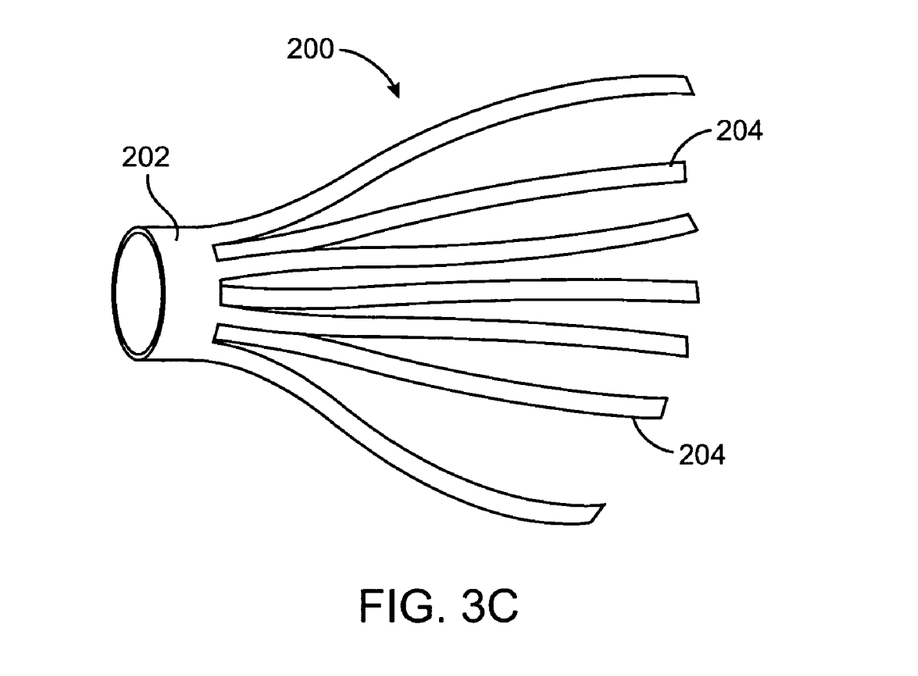

FIGS. 3A–3C show embodiments of a strut assembly for a percutaneously delivered temporary valve made in accordance with the present invention. In this embodiment, the strut assembly comprises a strut collar and a plurality of struts. The strut assembly provides improved fabrication and assembly. The strut assembly can be manufactured from a single piece of tubing. The strut assembly can be placed on the elongate element in a single operation, installing all the struts at once, rather than one at a time.

FIG. 3A shows a strut assembly in the fully formed configuration. The strut assembly 200 comprises a strut collar 202 and struts 204. The flexibility of the struts 204 allows the struts 204 to be compressed for introduction into the body lumen, to expand on release, and to alternately block and allow blood flow. In one embodiment, the strut collar 202 and struts 204 are one piece. In another embodiment, the struts 204 can be fabricated individually and attached to the strut collar 202. The strut collar 202 can be installed on the elongate element (not shown), before or after the membrane forming the temporary valve is attached to the struts 204. Dimples, cuts, or slots can be formed in the strut collar 202 so that the strut collar 202 attaches firmly to the elongate element. The struts 204 can have the same flexibility, or can have various flexibilities. Flexibility can be varied by the material properties and treatment, strut thickness, or a combination thereof.

FIG. 3B shows a strut assembly in the cut, but unformed, configuration. In one embodiment, the strut assembly 200 is cut from a nitinol shape metal alloy tube with a laser cutter or electrical discharge machining (EDM). The angle between the strut collar 202 and the struts 204, plus any shaping of the struts 204, can be performed by heat setting.

FIG. 3C shows a strut assembly having curved struts in a formed configuration. In this embodiment, the struts 204 have a soft S-shaped curve. The S-shaped curve is parallel or nearly parallel the vessel at the free end of the struts 204 and so provides an increased vessel contact area during use. The S-shaped curve also provides good outward spring, since the struts are parallel or nearly parallel the strut collar 202 where the struts 204 attach to the strut collar 202. The strut assembly 200 can be cut from a single nitinol shape metal alloy tube and the struts 204 formed by heat setting. Those skilled in the art will appreciate that a number of shapes can be used for the struts 204, such as straight, concave, convex, S-shaped, sigmoidal, or any combination thereof. In one embodiment, the struts 204 can be straight along most of their length, ending in a medially-concave bend a the distal end to reduce wear on the luminal surface of the aorta.

Figure 4:
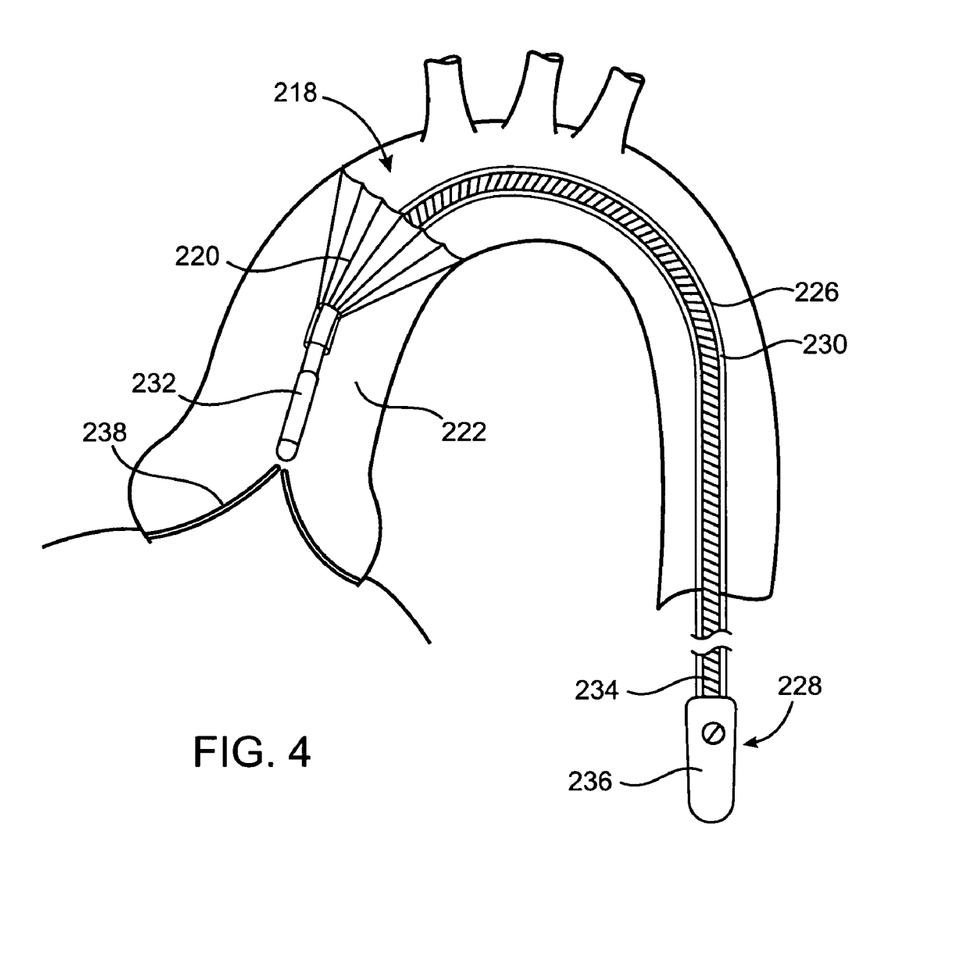
FIG. 4 shows a percutaneously delivered temporary valve having a central lumen made in accordance with the present invention.

FIG. 4 shows a percutaneously delivered temporary valve having a central lumen made in accordance with the present invention. The central lumen allows a tool to pass the temporary valve and reach a work area, such as a heart valve.

The temporary valve system 218 comprises a temporary valve 220 disposed on an elongate element 226, the elongate element 226 having a lumen 230. The temporary valve 220 can be located in the ascending aortic arch 222. The elongate element 226, shown cut away to reveal tool assembly 228, has a lumen 230 for passage of the tool assembly 228 past the temporary valve 220 to the work area, such as at the aortic valve 238. The tool assembly 228 comprises a tool 232, a shaft 234, and a tool connection 236. The tool assembly 228 can be any device required to carry out a percutaneous procedure, such as a catheter, an imaging device, a valve resection device, a replacement valve carrying device, or the like.

In this example, the temporary valve system 218 is used in replacement of a native aortic valve with a prosthetic aortic valve. An incision is made inguinally and the temporary valve system 218 advanced through the femoral artery until the temporary valve 220 is located in the ascending aorta 222. In one embodiment, the temporary valve system 218 can be introduced through a catheter. The temporary valve 220 is deployed from a collapsed state used for insertion to a deployed state in which the temporary valve 220 alternately opens and closes to block and allow blood flow. A valve resection tool is advanced through the lumen 230 of the elongate element 226, the native aortic valve is removed, and the valve resection tool is withdrawn. With no aortic valve present, the temporary valve 220 provides valve function. A valve implantation tool is advanced through the lumen 230 of the elongate element 226, the prosthetic aortic valve is installed, and the valve implantation tool is withdrawn. In one embodiment, the temporary valve 220 can be placed in the collapsed state and the temporary valve system 218 withdrawn from the patient. In another embodiment, the temporary valve system 218 can be left in place for days or weeks while the permanent prosthetic aortic valve heals in place, the temporary valve 220 relieving load on the prosthetic aortic valve during the healing process. After the healing is sufficient, the temporary valve 220 can be placed in the collapsed state and the temporary valve system 218 withdrawn from the patient.

Figure 5A:
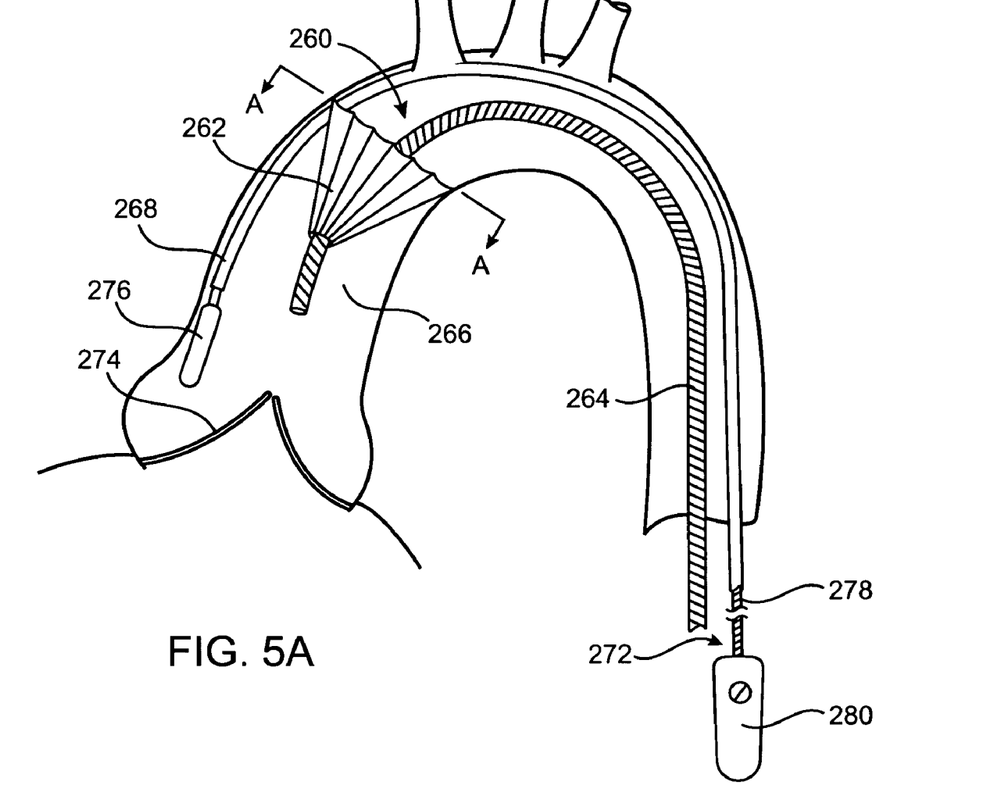
FIGS. 5A & 5B show a side and axial view, respectively, of a percutaneously delivered temporary valve with a separate bypass catheter and made in accordance with the present invention.
Figure 5B:
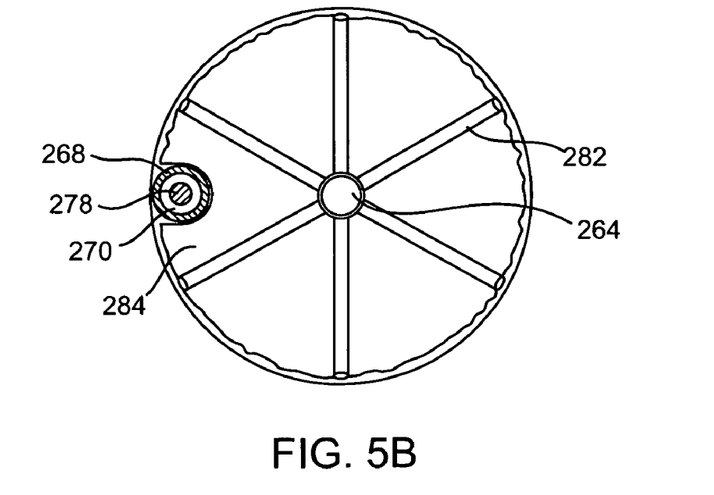

FIGS. 5A & 5B show a side and axial view, respectively, of a percutaneously delivered temporary valve with a separate bypass catheter and made in accordance with the present invention. The separate bypass catheter allows a tool to pass the temporary valve and reach a work area, such as a heart valve.

The temporary valve system 260 comprises a temporary valve 262 disposed on an elongate element 264. The temporary valve 262 can be located in the ascending aortic arch 266. A bypass catheter 268 is installed in the vessel parallel to the temporary valve system 260. The bypass catheter 268 has a lumen 270 for passage of the tool assembly 272 past the temporary valve 262 to the work area, such as at the aortic valve 274. In one embodiment, the elongate element 264 can also have at least one lumen so that multiple tools can be used in the work area at one time. The tool assembly 272 comprises a tool 276, a shaft 278, and a tool connection 280. The tool assembly 272 can be any device required to carry out a percutaneous procedure, such as a catheter, an imaging device, a valve resection device, a replacement valve carrying device, or the like.

FIG. 5B shows the axial view at section A—A of FIG. 5A with the temporary valve expanded and blocking flow during diastole. The struts 282 are spread out from the elongate element 264 and the membrane 284 blocks flow. The bypass catheter 268 passes between the struts 282 and the membrane 284 enfolds the bypass catheter 268 to prevent substantial flow along the outside of the bypass catheter 268.

In this example, the temporary valve system 260 is used in replacement of a native aortic valve with a prosthetic aortic valve. An incision is made inguinally and the bypass catheter 268 advanced through the femoral artery until the distal end is near the work area at the aortic valve 274. The temporary valve system 260 is advanced through the femoral artery until the temporary valve 262 is located in the ascending aorta 266. In one embodiment, the temporary valve system 260 can be introduced through a catheter. In another embodiment, the elongate member 264 of the temporary valve system 260 can include a lumen for introduction of additional tools to be used during the operation. The temporary valve 262 is deployed from a collapsed state used for insertion to a deployed state in which the temporary valve 262 alternately opens and closes to block and allow blood flow. A valve resection tool is advanced through the lumen 270 of the bypass catheter 268, the native aortic valve is removed, and the valve resection tool is withdrawn. With no aortic valve present, the temporary valve 262 provides valve function.

A valve implantation tool is advanced through the lumen 270 of the bypass catheter 268, the prosthetic aortic valve is installed, and the valve implantation tool is withdrawn. In one embodiment, the temporary valve 262 can be placed in the collapsed state, the temporary valve system 260 withdrawn from the patient, and the bypass catheter 268 withdrawn from the patient. In another embodiment, the bypass catheter 268 can be withdrawn from the patient and the temporary valve system 260 can be left in place for days or weeks while the prosthetic aortic valve heals in place, the temporary valve 262 relieving the load on the prosthetic aortic valve during the healing process. After the healing is sufficient, the temporary valve 262 can be returned to the collapsed configuration and the temporary valve system 260 withdrawn from the patient. Use of the temporary valve 262 during the healing process can allow use of a sutureless prosthetic valve, rather than a prosthetic valve requiring a sewing cuff and multiple knotted sutures to anchor the prosthetic valve until ingrowth of scar tissue occurs. This can reduce the time required and degree of difficulty of the valve replacement procedure.

Figure 6A:
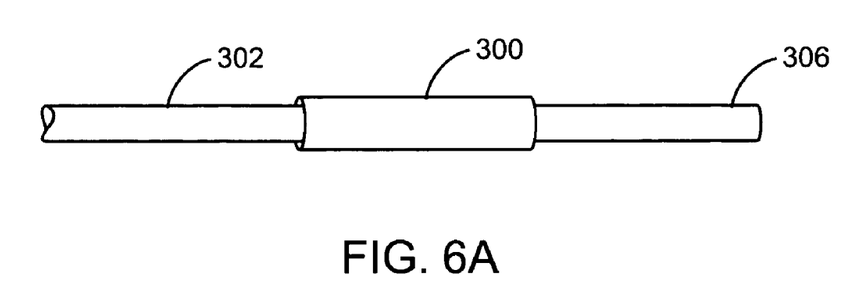
FIGS. 6A & 6B show a deployment system for a temporary valve in the collapsed and deployed state, respectively, for a percutaneously delivered temporary valve made in accordance with the present invention.
Figure 6B:
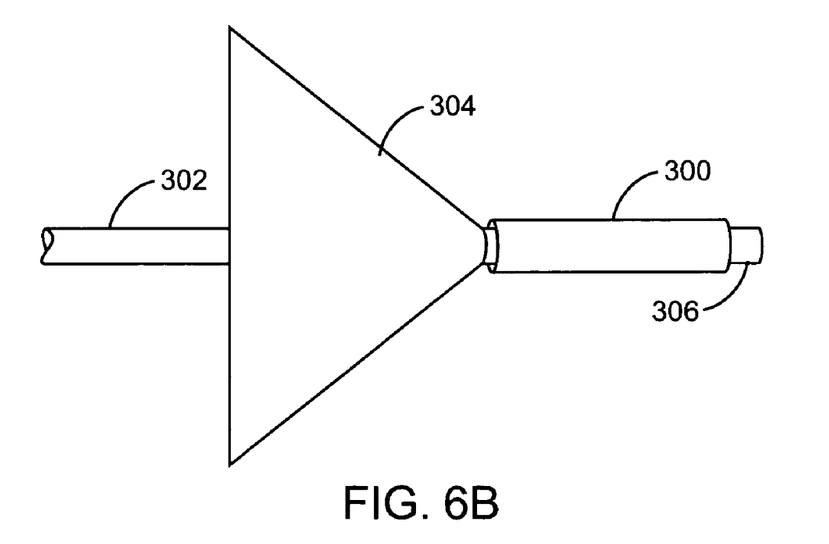

FIGS. 6A & 6B show a deployment system for a temporary valve in the collapsed and deployed state, respectively, for a percutaneously delivered temporary valve made in accordance with the present invention. In this example, a moveable sheath is employed to restrain the temporary valve during insertion into and withdrawal from the patient.

FIG. 6A shows a sheath 300 slidably mounted along the elongate body 302 at the distal tip 306 of a temporary valve system. FIG. 6B shows the sheath 300 moved toward the distal tip 306 of the elongate body 302, deploying the temporary valve 304. The sheath 300 maintains the temporary valve 304 in a collapsed state so the temporary valve 304 can be moved through a body lumen to the point of use. In one embodiment, the sheath 300 completely covers the temporary valve 304. In another embodiment, the sheath 300 partially covers the temporary valve 304. The sheath 300 can be moved by a wire (not shown) within a lumen of the elongate body 302. The wire pushes the sheath 300 toward the distal tip 306 of the elongate body 302 to deploy the temporary valve 304 for use. The wire pulls the sheath 300 away from the distal tip 306 of the elongate body 302 to collapse the temporary valve 304 for withdrawal. Those skilled in the art will appreciate that numerous mechanisms are possible to shift the temporary valve between the deployed and collapsed state.

Figure 7:
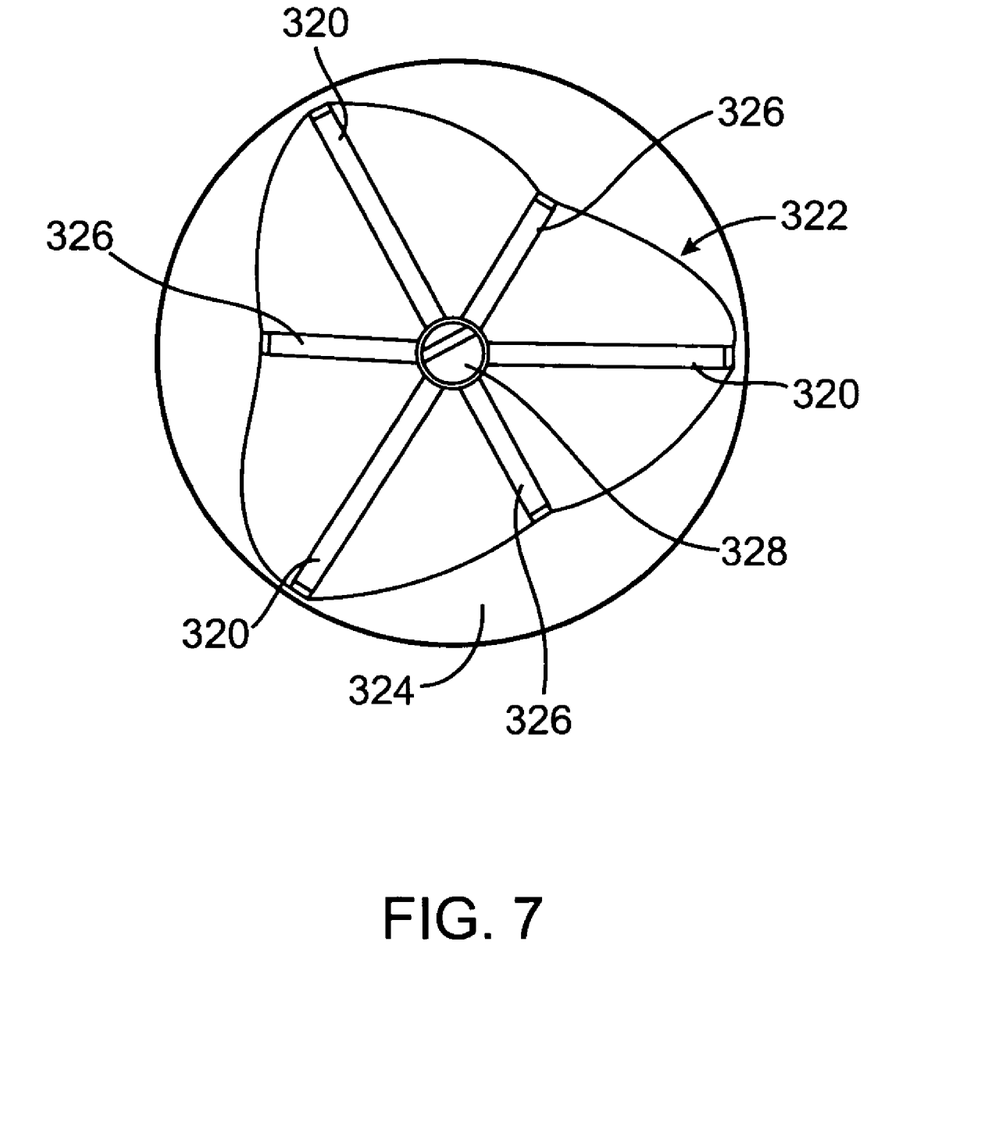
FIG. 7 shows an axial view of a percutaneously delivered temporary valve having mixed stiffness struts made in accordance with the present invention.

FIG. 7 shows an axial view of a percutaneously delivered temporary valve having mixed stiffness struts made in accordance with the present invention. The temporary valve 322 is shown permitting flow through the body lumen 324. In this example, the struts are divided into two groups, centering struts 320 to maintain the temporary valve 322 centered within the body lumen 324 and flow struts 326 to allow flow past the temporary valve 322. In this example, the centering struts 320 alternate with the flow struts 326. Optionally, the strut pattern could be selected to fit a particular application, e.g., two centering struts could be provided for every flow strut to hold the temporary valve more firmly, or two flow struts could be provided for every flow strut to assure greater flow. The centering struts 320 are relatively stiff and do not move with the pumping of the heart. The flow struts 326 are relatively flexible, bending in toward and out away from the elongate member 328 to alternately allow and block flow.

Figure 8A:
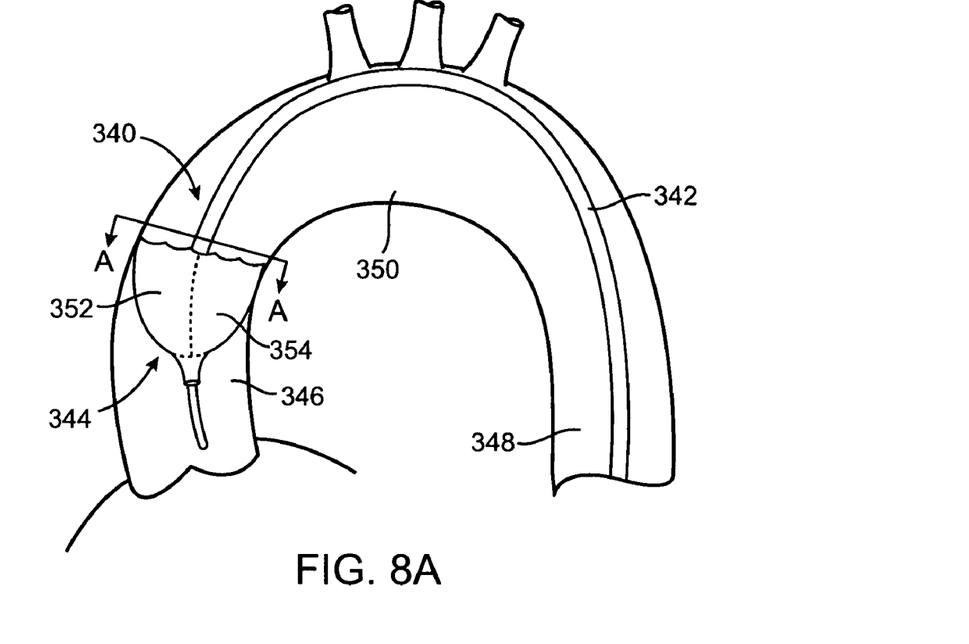
FIGS. 8A & 8B show a side and axial view, respectively, of a percutaneously delivered temporary valve having mixed stiffness strut groups made in accordance with the present invention.
Figure 8B:
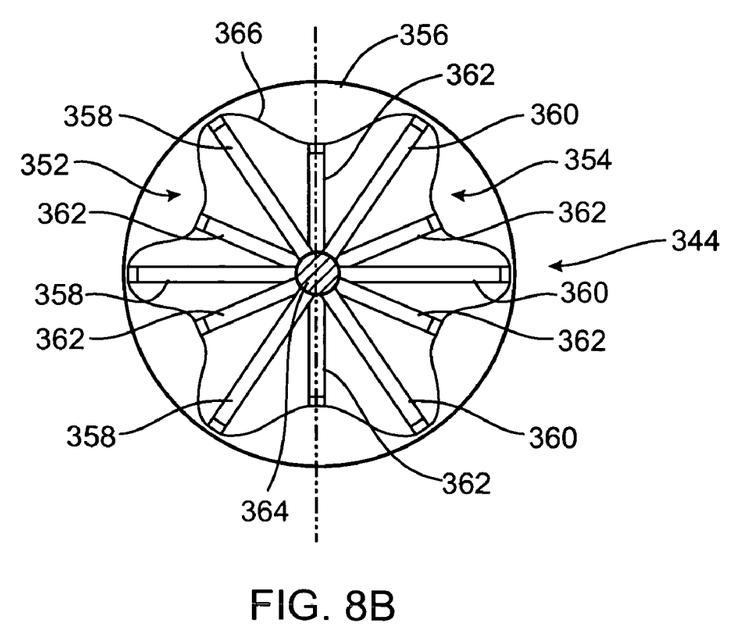

FIGS. 8A & 8B show a side and axial view, respectively, of a percutaneously delivered temporary valve having mixed stiffness strut groups made in accordance with the present invention. Mixed stiffness strut groups can be used to allow for the difference in force on the temporary valves from flexure of the elongate element or characteristics of the body lumen for a particular patient. The temporary valve comprises at least a first region and a second region, and the centering struts in the first region have a first stiffness and the centering struts in the second region have a second stiffness. Different patients have different aorta dimensions, so it is desirable to fit the temporary valve to a particular patient's characteristics.

FIG. 8A shows a temporary valve assembly 340, comprising an elongate member 342 and a temporary valve 344, with the temporary valve 344 located in the ascending aorta 346. The elongate member 342 can be preformed to ease insertion in the path around the bend from the descending aorta 348 through the aortic arch 350 into the ascending aorta 346. However, the severity of the bend will cause the elongate member 342 to apply more force on the temporary valve outer region 352 and less force on the temporary valve inner region 354, tending to move the elongate member 342 off center. This will decrease the effectiveness of the temporary valve 344 and result in the temporary valve 344 shifting within the ascending aorta 346 as the heart beats. The strut characteristics for the inner and outer regions can be selected to account for the force difference.

FIG. 8B shows an axial view of the temporary valve 344 from FIG. 8A at the section A—A, the temporary valve 344 is shown permitting flow through the body lumen 356. The temporary valve 344 comprises a membrane 366, inner centering struts 360, outer centering struts 358, and flow struts 362. The centering struts 360, 358 maintain contact with the vessel wall to center the elongate element 342, and the flow struts 362 control flow through the temporary valve 344. In this example, the design of the centering struts in the temporary valve outer region 352 and the temporary valve inner region 354 are different to account for the force difference from the elongate member 342. The outer centering struts 358 are stiffer to resist the greater force, while the inner centering struts 360 are more flexible to resist the lesser force. The flow struts 362 are even more flexible, bending in toward and out away from the elongate member 364 to alternately allow and block flow. The desired strut stiffness can be obtained by the strut thickness, material characteristics, or a combination thereof.

Those skilled in the art will appreciate that the strut characteristics can be selected to provide additional design options. In one embodiment, the centering struts can be grouped in thirds of the temporary valve, with the centering struts in one third having a different stiffness from the other two thirds, or with the centering struts in each of the thirds having a different stiffness. In another embodiment, the centering struts can be grouped in quarters of the temporary valve, with a selected stiffness for each of the quarters.

Figure 9:
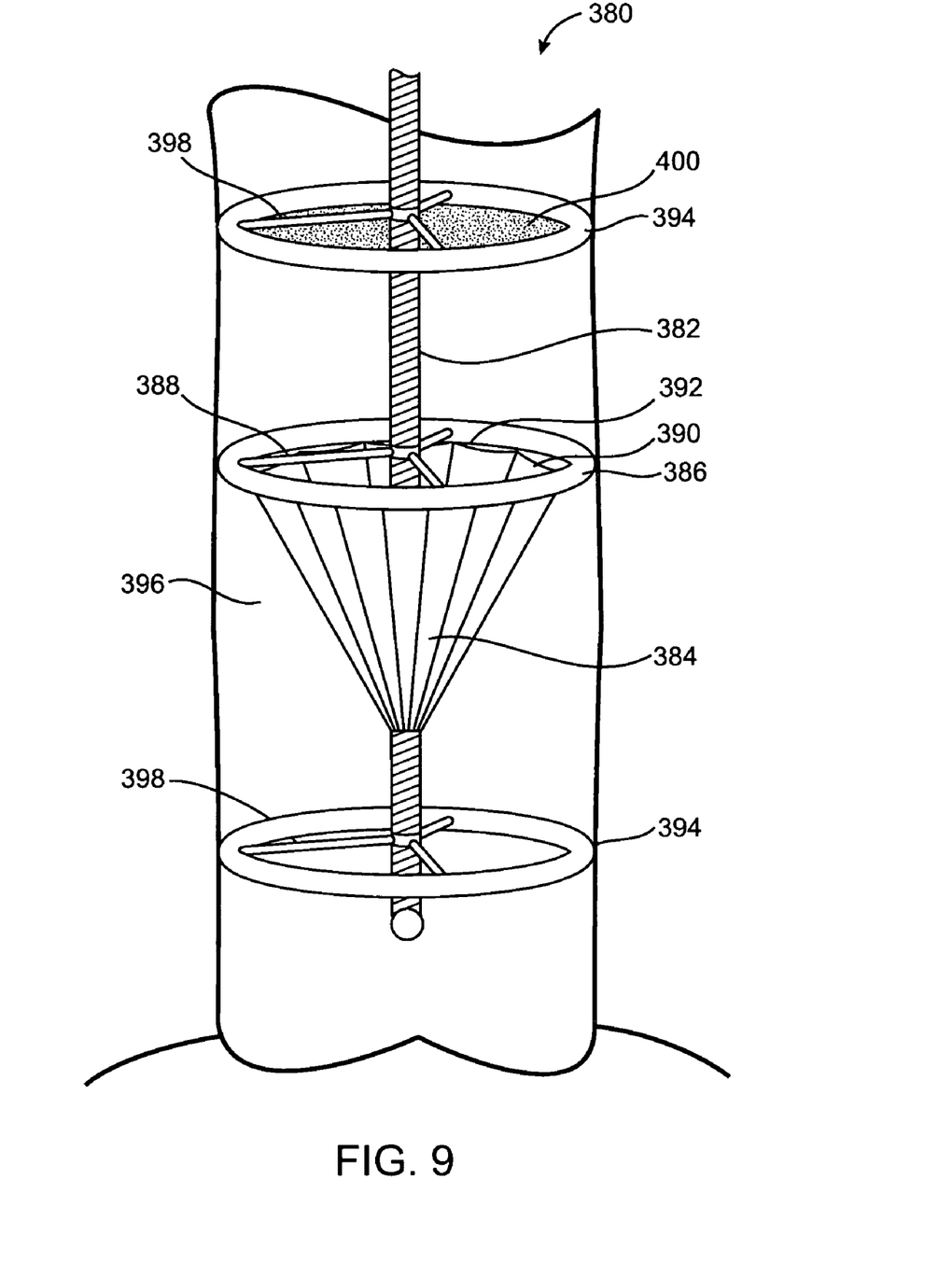
FIG. 9 shows a percutaneously delivered temporary valve having centering balloons made in accordance with the present invention.

FIG. 9 shows a percutaneously delivered temporary valve having centering balloons made in accordance with the present invention. The temporary valve assembly 380 comprises an elongate member 382, a temporary valve 384 disposed on the elongate member 382, and a centering balloon 386 supported by braces 388. The braces 388 are collapsible, and include a passage (not shown) communicating between a lumen in the elongate member 382 and the interior of the centering balloon 386 for inflation of the centering balloon 386. In one embodiment, the braces 388 are made of the same material and are integral to the centering balloon 386. The braces 388 inflate with the centering balloon 386. In another embodiment, the braces 388 are made of a metal, such as stainless steel or a shape metal alloy like nitinol. The centering balloon 386 can be manufactured from a material such as polyethylene, polyethylene terephthalate (PET), nylon, Pebax® polyether-block co-polyamide polymers, or the like.

The seating edge 390 of the temporary valve 384 is aligned with the inner edge 392 of the centering balloon 386. The vessel wall is protected from impact with the temporary valve 384 as the temporary valve 384 alternately moves to block and allow flow, because the seating edge 390 contacts the centering balloon 386, rather than the vessel wall. The mating surfaces of the seating edge 390 and the inner edge 392 can be designed to provide a superior seal.

In one embodiment, one or more auxiliary centering balloons 394 can be disposed along the elongate member 382 of the temporary valve assembly 380 to center the elongate member 382 within the body lumen 396. The auxiliary centering balloons 394 can be placed proximally or distally of the temporary valve 384. The auxiliary braces 398 are collapsible, and include a passage (not shown) communicating between a lumen in the elongate member 382 and the interior of the auxiliary centering balloons 394 for inflation of the auxiliary centering balloons 394. In one embodiment, the auxiliary braces 398 are made of the same material and are integral to the auxiliary centering balloon 394. The auxiliary braces 398 inflate with the auxiliary centering balloon 394. In another embodiment, the auxiliary braces 398 are made of a metal, such as stainless steel or a shape metal alloy like nitinol. The auxiliary centering balloon 394 can be manufactured from a material such as polyethylene, polyethylene terephthalate (PET), nylon, Pebax® polyether-block co-polyamide polymers, or the like. Those skilled in the art will appreciate that the elongate member can be centered using other elements attached to the elongate member, such as radially projecting collapsible fingers, springs, or the like.

Filter material 400 can be connected across opening in the auxiliary centering balloon 394 to remove embolic material during an operation. For aortic valve operations, placement of the auxiliary centering balloon 394 including filter material 400 upstream of the brachiocephalic artery prevents embolic material from entering the arteries branching from the aortic arch, reducing the risk of stroke. The filter material 400 can be any non-thrombogenic mesh, such as polyethylene mesh, Dacron polyester mesh, nylon mesh, textile fabrics, spun bonded polyolefin, expanded polytetrafluoroethylene, or nonwoven materials. The pore size of the filter material 400 can be of a size sufficient to block and capture any micro- and macro-emboli which may flow downstream from the site of the operation, but large enough that blood flow is not impeded. The pore size can be less than about 500 microns, typically about 50 to 250 microns. In another embodiment, a separate filtering device, such as the Scion Cardio-Vascular SCI-PRO® guide wire based retrieval device from Scion Cardio-Vascular, Inc., of Miami, Fla., can be inserted in parallel with the temporary valve assembly to remove embolic material during an operation.

Figure 10A:
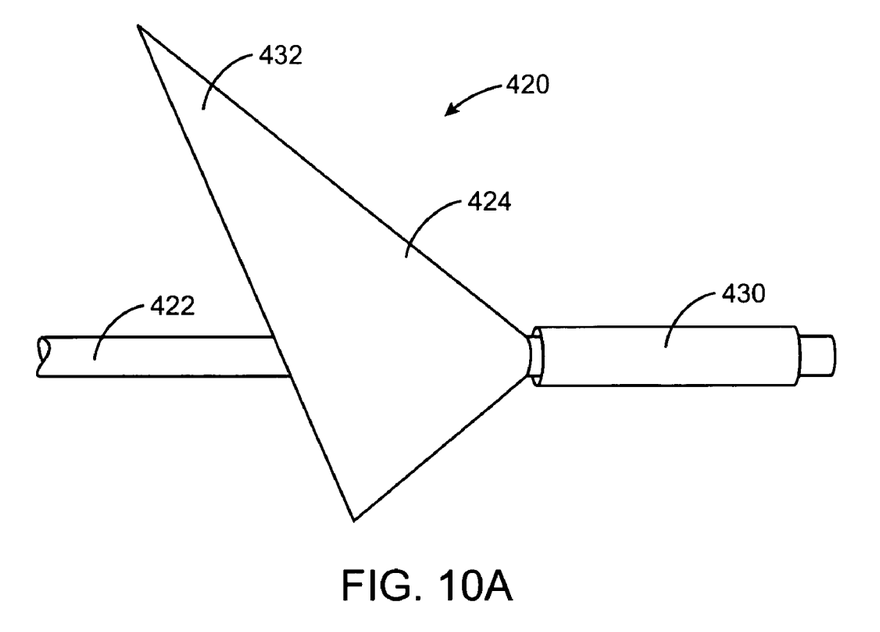
FIGS. 10A & 10B show a side and axial view, respectively, of an eccentric percutaneously delivered temporary valve made in accordance with the present invention.
Figure 10B:
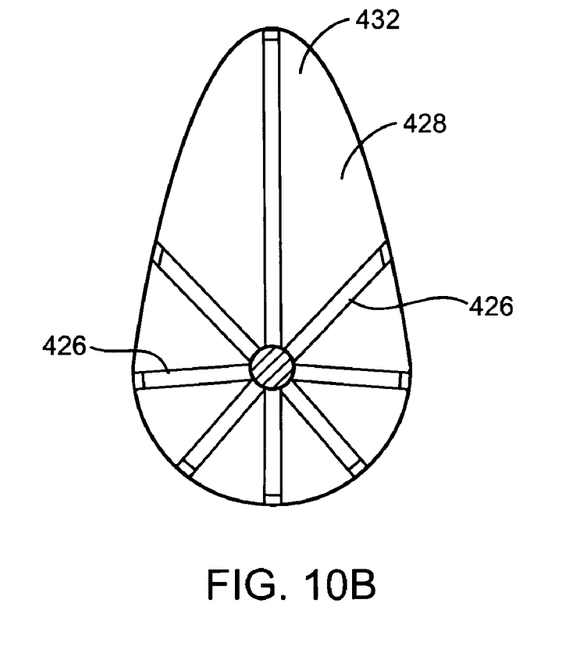

FIGS. 10A & 10B show a side and axial view, respectively, of an eccentric percutaneously delivered temporary valve made in accordance with the present invention. The irregular shape of the temporary valve provides a custom fit depending on the body lumen geometry of a particular patient. The temporary valve assembly 420 comprises an elongate element 422 and a temporary valve 424, the temporary valve 424 further comprising struts 426 and a membrane 428. A moveable sheath 430 can be slidably mounted on the elongate element 422 to cover the temporary valve 424 while the temporary valve assembly 420 is moved through a body lumen. The eccentric lobe 432 of the temporary valve 424 can be disposed against the outer curve of the ascending aorta to increase the contact area with the outer vessel wall. In another embodiment, the temporary valve can be elliptical to orient the elongate element at an angle relative to the axis of the body lumen. Those skilled in the art will appreciate that the temporary valve 424 can be different shapes and sizes to fit the varied anatomies of different patients.

Figure 11:
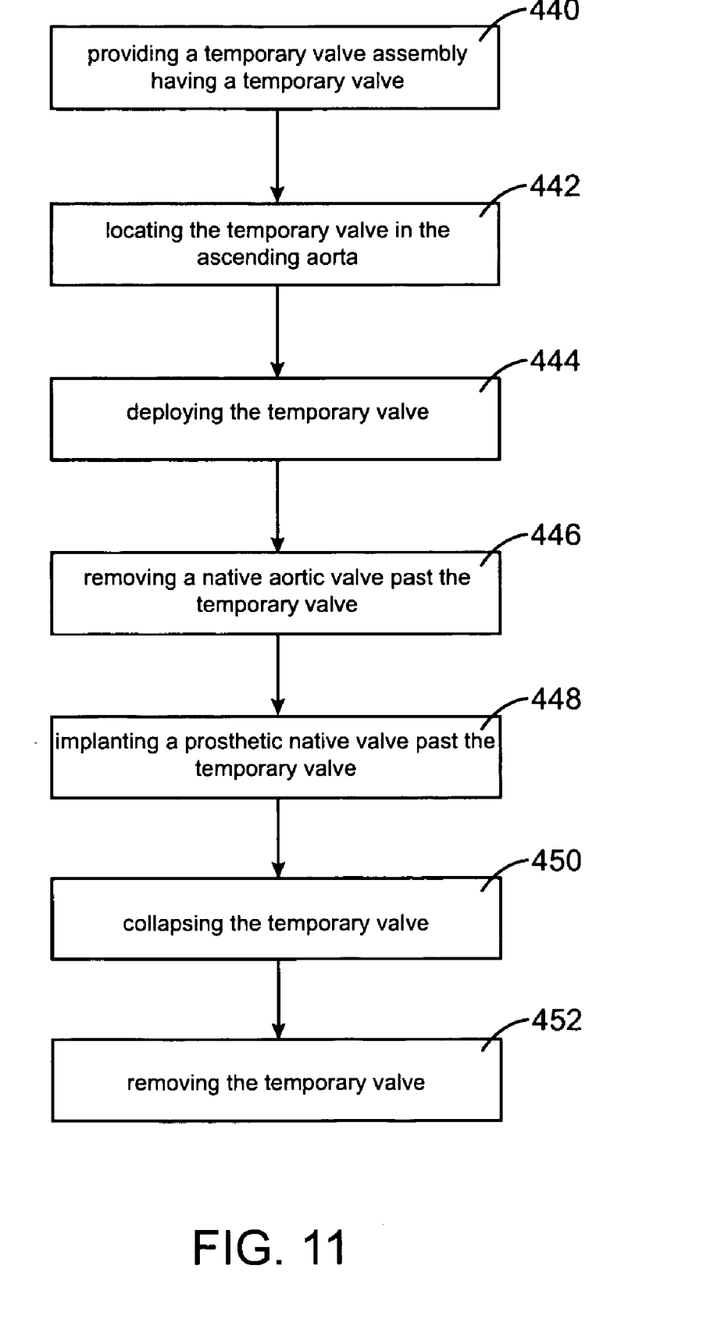
FIG. 11 shows a flow chart for a method of use for a percutaneously delivered temporary valve made in accordance with the present invention.

FIG. 11 shows a flow chart for a method of use for a percutaneously delivered temporary valve made in accordance with the present invention. At 440, a temporary valve assembly is provided, the temporary valve assembly comprising an elongate element and a temporary valve disposed near the distal end of the elongate element, the elongate element including a lumen. In one embodiment, the temporary valve can be sized to a particular patient. The temporary valve assembly is inserted into the patient so the temporary valve is located in the ascending aorta of the patient 442. In one embodiment, the temporary valve can be sized to the particular patient by trial fitting in the ascending aorta. In another embodiment, the temporary valve can be sized to the particular patient by pre-measuring the patient. The temporary valve is deployed 444. The native aortic valve is removed past the temporary valve through the lumen of the elongate element 446 and a prosthetic aortic valve implanted past the temporary valve through the lumen of the elongate element 448. The temporary valve is collapsed 450 and the temporary valve assembly removed from the patient 452. In one embodiment, the temporary valve assembly can be retained in the patient until the prosthetic aortic valve heals in and temporary valve assembly removed after a few days or weeks. In one embodiment, the temporary valve assembly can be removed immediately.

It is important to note that FIGS. 1–11 illustrate specific applications and embodiments of the present invention, and is not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A temporary valve system comprising:
    an elongate element; and
    a temporary valve disposed on the elongate element, the temporary valve comprising struts and a membrane attached to the struts; and
    the struts further comprising centering struts and flow struts.

2. The temporary valve system of claim 1 wherein the elongate element includes at least one lumen.

3. The temporary valve system of claim 1, the temporary valve further comprising a seating edge and a skirt attached to the seating edge.

4. The temporary valve system of claim 1 wherein the membrane is coated with an anti-thrombotic material.

5. The temporary valve system of claim 1 wherein the struts are attached to a strut collar, the strut collar being disposed about the elongate element.

6. The temporary valve system of claim 5 wherein the strut collar and struts are a single piece.

7. The temporary valve system of claim 1 wherein strut shape is selected from the group consisting of straight, concave, convex, S-shaped, sigmoidal, and combinations thereof.

8. The temporary valve system of claim 1 wherein the elongate element has a long axis and a distal tip, and the distal tip is angled with respect to the long axis.

9. The temporary valve system of claim 1 wherein the elongate element has a distal tip, and the distal tip is steerable.

10. The temporary valve system of claim 1 wherein the elongate element has a distal tip, and the temporary valve is a distance from the distal tip that locates the temporary valve in an ascending aorta during use.

11. The temporary valve system of claim 1 wherein the elongate element has a distal tip, and the temporary valve is between about 1 and 8 centimeters from the distal tip.

12. The temporary valve system of claim 11 wherein the temporary valve is about 5 centimeters from the distal tip.

13. The temporary valve system of claim 1 further comprising means for deploying the temporary valve.

14. The temporary valve system of claim 1 further comprising a sheath, the heath being slidably mounted along the elongate body, the sheath having a first position and a second position, wherein the sheath at least partially covers the temporary valve in the first position and the sheath deploys the temporary valve in the second position.

15. The temporary valve system of claim 1 wherein the centering struts alternate with the flow struts.

16. The temporary valve system of claim 1 wherein the temporary valve comprises at least a first region and a second region, and the centering struts in the first region have a first stiffness and the centering struts in the second region have a second stiffness.

17. The temporary valve system of claim 1 further comprising means for centering the elongate member in a body lumen.

18. The temporary valve system of claim 1 further comprising a centering balloon, the centering balloon being disposed on the elongate member.

19. The temporary valve system of claim 18 wherein the temporary valve has a seating edge, the seating edge being aligned to contact the centering balloon.

20. The temporary valve system of claim 18 wherein the centering balloon includes an opening, the opening being covered with filter material.

21. The temporary valve system of claim 1 wherein the temporary valve is eccentric.

22. The temporary valve system of claim 1 further comprising a bypass catheter, the bypass catheter being locatable between the struts.

23. The temporary valve system comprising:
    a elongate element, the elongate element including at least one lumen; and
    an umbrella-like temporary valve having centering struts and flow struts, the umbrella-like temporary valve disposed on the elongate element.

24. The temporary valve system of claim 23, the temporary valve further comprising a seating edge and a skirt attached to the seating edge.

25. The temporary valve system of claim 23 wherein the temporary valve is coated with an anti-thrombotic material.

26. The temporary valve system of claim 23 wherein the elongate element has a long axis and a distal tip, and the distal tip is angles with respect to the long axis.

27. The temporary valve system of claim 23 wherein the elongate element has a distal tip, and the distal tip is steerable.

28. The temporary valve system of claim 23 wherein the elongate element has a distal tip, and the temporary valve is a distance from the distal tip that locates the temporary valve in an ascending aorta during use.

29. The temporary valve system of claim 23 further comprising means for deploying the temporary valve.

30. The temporary valve system of claim 23 further comprising a sheath, the sheath being slidably mounted along the elongate body, the sheath having a first position and a second position, wherein the sheath at least partially covers the temporary valve in the first position and the sheath deploys the temporary valve in the second position.

31. The temporary valve system of claim 23 further comprising means for centering the elongate member in a body lumen.

32. The temporary valve system of claim 23 further comprising a centering balloon, the centering balloon being disposed on the elongate member.

33. The temporary valve system of claim 32 wherein the temporary valve has a seating edge, the seating edge being aligned to contact the centering balloon.

34. The temporary valve system of claim 32 wherein the centering balloon includes an opening, the opening being covered with filter material.

35. The temporary valve system of claim 23 wherein the temporary valve is eccentric.

36. A method for replacing a native aortic valve with a prosthetic aortic valve in a patient comprising:
   providing a temporary valve assembly having an elongate element having a temporary valve disposed on the elongate element, the temporary valve comprising struts and a membrane attached to the struts; and the struts further comprising centering struts and flow struts;
   sizing the temporary valve to the patient;
   locating the temporary valve in an ascending aorta of the patient;
   deploying the temporary valve;
   removing the native aortic valve past the temporary valve;
   implanting the prosthetic aortic valve past the temporary valve;
   collapsing the temporary valve; and
   removing the temporary valve from the patient.

37. The method of claim 36 wherein sizing the temporary valve to the patient comprises trial fitting the temporary valve.

38. The method of claim 36 wherein sizing the temporary valve to the patient comprises pre-measuring the patient.

* * * * *